US006813376B1

(12) United States Patent
Hennessey et al.

(10) Patent No.: US 6,813,376 B1
(45) Date of Patent: Nov. 2, 2004

(54) SYSTEM AND METHOD FOR DETECTING DEFECTS ON A STRUCTURE-BEARING SURFACE USING OPTICAL INSPECTION

(75) Inventors: Kathleen Hennessey, Richardson, TX (US); Youling Lin, Richardson, TX (US); Yongqiang Liu, Plano, TX (US); Veera V. S. Khaja, Plano, TX (US); Yonghang Fu, Plano, TX (US)

(73) Assignee: Rudolph Technologies, Inc., Flanders, NJ (US)

( * ) Notice: Subject to any disclaimer, the term of this patent is extended or adjusted under 35 U.S.C. 154(b) by 643 days.

(21) Appl. No.: 09/697,807

(22) Filed: Oct. 27, 2000

Related U.S. Application Data
(60) Provisional application No. 60/162,399, filed on Oct. 29, 1999.

(51) Int. Cl.[7] .......................... G06K 9/00; G01N 21/00; H01L 21/66
(52) U.S. Cl. ...................... 382/145; 382/149; 382/151; 356/237.2; 356/237.5; 257/E21.53; 438/16
(58) Field of Search ................................ 382/141, 144, 382/145, 147, 149, 151; 356/237.2, 237.3, 237.4, 237.5; 257/E21.527, E21.53; 438/16

(56) References Cited

U.S. PATENT DOCUMENTS

| | | | | |
|---|---|---|---|---|
| 4,047,154 A | * | 9/1977 | Vitols et al. | 382/125 |
| 4,254,400 A | * | 3/1981 | Yoda et al. | 382/194 |
| 4,567,610 A | * | 1/1986 | McConnell | 382/170 |
| 4,581,762 A | * | 4/1986 | Lapidus et al. | 382/263 |
| 5,515,453 A | * | 5/1996 | Hennessey et al. | 382/141 |
| 5,586,199 A | * | 12/1996 | Kanda et al. | 382/197 |
| 5,602,401 A | * | 2/1997 | Broude et al. | 250/559.45 |
| 6,091,846 A | * | 7/2000 | Lin et al. | 382/145 |
| 6,137,893 A | * | 10/2000 | Michael et al. | 382/103 |

* cited by examiner

*Primary Examiner*—Jingge Wu
*Assistant Examiner*—Ryan J. Hesseltine

(57) ABSTRACT

A method of collating and using captured semiconductor-wafer image data in an automated defect analysis. The method includes the steps of receiving image data and, if necessary, converting it to a digital format. Once the data is in pixel-by-pixel form, each pixel is assigned a slope value derived from the direction of the structure edge, if any, on which it lies. The pixel-slope data is then evaluated to determine whether a photo-resist anomaly is present. The method may also include evaluated an average pixel slope value for each inspected wafer. Dependant claims further define the invention to claim an inspection system for employing the method.

3 Claims, 6 Drawing Sheets

SYSTEM AND METHOD FOR DETECTING DEFECTS ON A STRUCTURE-BEARING SURFACE USING OPTICAL INSPECTION

RELATED APPLICATIONS

This application is related to and claims the benefit of the filing date of U.S. Provisional Application No. 60/162,399, filed Oct. 29, 1999. This application is also related to U.S. patent applications Ser. Nos. 09/262,6030, U.S. Pat. Nos. 6,487,307 and 09/338,880, U.S. Pat. No. 6,292,260, filed Mar. 4, 1999 and Jun. 23, 1999, respectively. Each of these applications is incorporated in their entirety herein by reference.

BACKGROUND OF THE INVENTION

1. Technical Field of the Invention

The present invention relates to automated optical inspection systems, and, more specifically, to a system and method for detecting and classifying semiconductor-wafer surface defects related to the deposition of photoresist during the manufacturing process.

2. Description of Related Art

Optical inspection is a widely used method of non-destructive testing for defects visibly present at or near the surface of an article of manufacture. Optical inspection encompasses a variety of techniques that make use of the patterns produced by energy reflecting off (or passing through) the object being inspected. These reflections constitute an image that can be captured, stored, digitized, examined, compared with other images, and otherwise analyzed. Any defects discovered by the inspection process can then be further analyzed and classified so that, where possible, repairs can be performed either immediately or at some time in the future, and similar defects avoided.

Although applicable in a variety of contexts, the method of the present invention is of particular advantage when applied to the optical inspection of semiconductor wafers during the manufacturing process. Semiconductor wafers are slices of a semiconducting material, such as silicon, that are repeatedly coated, treated, and etched away in selected areas to form very small interconnected electronic devices, such as transistors. A set of thousands, even millions of these interconnected devices is called a "die". A single wafer can serve as the base for forming several, or even hundreds of such dice. After the dice are populated with electronic devices, they are separated and each is individually encased in a package to form what is commonly referred to as a "chip". Chips can contain a very large number of electrical circuits and are used in constructing a wide variety of electronic devices.

In order to transform a wafer into sets of electronic devices, the wafer undergoes several manufacturing steps. First, a wafer is cut from a crystal ingot (such as crystallized silicon), and an epitaxial layer (a single layer of silicon crystals) may typically be grown on it. The creation of an epitaxial layer is often followed by the growth of high quality oxides on the wafer surface in a process called oxidation. Next, the wafer undergoes several fabrication steps. Each fabrication step places a layer of ions or other materials into or on the wafer, or removes portions from it, in a predetermined geometric pattern so as to form a portion of an electronic circuit.

Common wafer fabrication steps include chemical vapor depositions (CVD), plasma-enhanced vapor depositions (PECVD), etches, ion implantations, diffusions, metalizations, or the growth of structures directly on the wafer. Naturally, these structures are quite small, and the successful completion of the fabrication steps depends largely on the ability to precisely control the geometric placement of gasses, ions, metals, or other deposition materials. The processes of etching, implanting, etc., must be done with sub-micron precision. The precise placement of ions, metals, gasses, or other deposits and removal of other materials is often achieved through a process called photolithography.

Photolithography is a process by which the wafer surface is selectively covered with a material called "photoresist" (or simply "resist") so that subsequent processes of ion implantation, etching, etc., effect only certain areas.

Photoresist is a light-sensitive material that is applied to the entire wafer surface, which is often spun rapidly to distribute the photoresist material evenly across the surface. The photoresist is then selectively exposed to a patterned light source at a predetermined wavelength. The mask's pattern, like a photographic negative, is projected onto one portion of the wafer at a time by a precision optical device known as a "stepper", and the pattern is preserved on each die by the photoresist. There are different kinds of photoresist used in wafer manufacture, each having different properties. "Positive" photoresist, for example, is made soluble by exposure to the light, while "negative" photoresist is hardened.

The next step in photolithography is called development, where the wafer is flushed with a solvent that washes away certain portions of the photoresist. Different types of solvents can be used. One solvent will wash away the portions of positive photoresist that were exposed to the light, while another washes away the unexposed portions of negative photoresist. In either case, the development process leaves the geometric pattern of the mask (or its negative) on each die. The result is a series of "photoresist structures" that together constitute a developed photoresist layer.

By selectively covering portions of the semiconductor wafer with photoresist structures, the entire wafer can, in a subsequent fabrication step, be exposed to various chemicals, ions, metals, or etchings without affecting the entire areas under the photoresist structures. After each fabrication step has been completed, a wash step is executed. In the wash step, all remaining photoresist is washed away and the wafer is cleaned. Often, one or more additional fabrication steps will be needed, and, the wafer will then undergo further photolithography processes.

As can readily be seen from this discussion, in order to correctly manufacture microelectronic devices, geometrically correct patterns of photoresist structures must be deposited on the wafer during fabrication. And correct geometric patterning is dependent upon properly imaging and developing photoresist layers.

Each fabrication step is expensive and adds significantly to the cost of the semiconductor wafer. Furthermore, fabrication steps such as etching and ion implantation are difficult, if not impossible, to reverse in any cost-effective way. By contrast, photoresist structures can be removed quickly and with minimal disturbance to the underlying wafer structures. Thus, it is desirable to detect defects in the developed photoresist prior to performing a fabrication step. Photoresist defects are those anomalies that will result in impaired or altered electrical characteristics when fabrication of the die is complete, causing it to be rejected. Common photoresist defects include alignment errors, missing photoresist structures, contamination, and skewed photoresist (such as streaking or ring anomolies).

If a defect can be detected in the developed photoresist layer prior to a fabrication step, one simply washes away the photoresist structures and develops another photoresist layer in place of the defective one. If the number of defects attributable to imperfections on the photoresist can be thereby reduced, the corresponding increase in die yield will result in considerable savings.

As mentioned above, the most common method used to detect imperfections in a developed photoresist layer is optical inspection. Other methods often used include electronic, ion beam, and X-ray imaging, although they are slower and more expensive than optical inspection because these imaging techniques illuminate and reconstruct only one point at a time. Laser imaging techniques that capture and compare the angle of reflection of laser beams can also be employed, but sacrifice comparable precision in reporting the position of defects. At any given wafer fabrication facility, however, there are likely to be a multitude of different inspection systems in use, each chosen for a specific purpose after weighing the costs and benefits relative to that particular function.

These numerous inspection systems are only one part of an overall quality control system. The other quality-control components in use may vary from site to site, but often include one or more review systems (through which a more detailed inspection can be performed), analysis and evaluation systems, repair systems, and databases for storing defect-related data.

Although the present invention may be utilized advantageously in numerous applications, the need for the present invention is apparent in the context of a typical optical wafer inspection system. Given the number of images that must be captured for adequate quality control in the manufacturing process, and the detail required for satisfactory inspection, the amount of data and the time it takes to transform and evaluate it can become enormous. The present invention provides an automatic inspection system and method that is both accurate and efficient is the detection and classification of defects.

SUMMARY OF THE INVENTION

The present invention provides a system and method for use in inspecting for defects on a structure-bearing surface of an object, for example, in photoresist structures on a semiconductor wafer. In one aspect of the invention, the method includes the steps of receiving data that has already been collected and converted to digital format, assigning a slope value to each pixel, and evaluating an arrangement of the pixel-slope data to locate anomalies. The method may also include the step of creating a visual graphic representation of the processed data.

In another aspect, the present invention is directed to a system for detecting defects on structure-bearing surfaces that performs the method of processing and analyzing the image data.

BRIEF DESCRIPTION OF THE DRAWINGS

The invention will be better understood and its numerous objects and advantages will become more apparent to those skilled in the art by reference to the following drawings, in conjunction with the accompanying specification, in which.

DETAILED DESCRIPTION OF A PREFERRED EMBODIMENT

The present invention provides a system and method for use in inspecting a structure-bearing surface of an object for defects. The preferred embodiment is described in the context of the inspections of photoresist structures on the surface of semiconductor wafers. Such inspections are routinely performed at numerous points during the process of fabrication.

Figure 1:
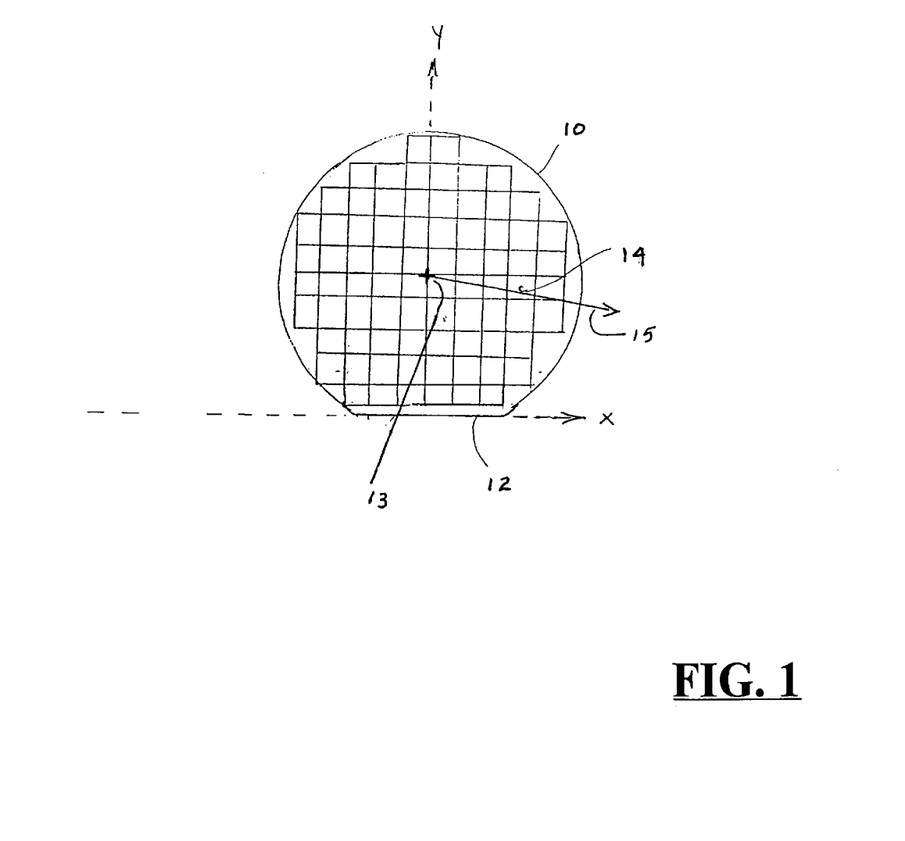
FIG. 1 is a drawing of a typical semiconductor wafer, such as one that may be subject to inspection according to the present invention.

FIG. 1 is a drawing of a typical semiconductor wafer 10, such as one that may be subject to inspection according to the present invention. This view of wafer 10 features the production surface, that is, the side of the wafer on which electrical devices are being constructed. Wafer 10 has a center 13 and from this perspective is generally round, but does have one straight edge this is referred to as a flat 12. As shown in FIG. 1, an x-y coordinate system can be defined by the flat, with the x-axis running along flat 12 and the y-axis perpendicular to it and passing through center 13. This convention will be used herein, and is convenient as photoresist structures typically have edges parallel or perpendicular to the flat. It should be apparent, however, that the selection of any other coordinate-axes orientation and origin will also enable practice of the present invention. Also, any number of vectors, such as vector 15 shown in FIG. 1, radiate from the center 13 of wafer 10 outward to the nearest point on the wafer periphery. (The x-y coordinate axes and vector 15 are not visible features of an actual wafer 10, of course, but are shown here to define them for the purpose of the defect analysis.)

Figure 2:
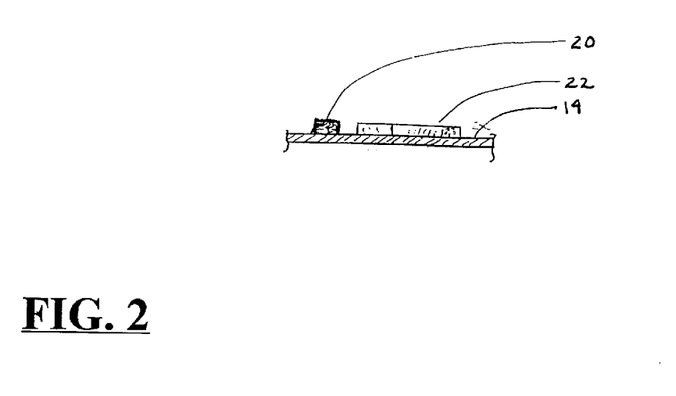
FIG. 2 is a cutaway elevation view of a die (not to scale) that forms part of the wafer shown in FIG. 1 to show photoresist structures.

The production surface of wafer 10 is divided into a plurality of dice, such as die 14. FIG. 2 is a cutaway elevation view of the portion of wafer 10 including die 14, shown bearing on its production surface two photoresist structures 20 and 22. (FIG. 2 is not drawn to scale—the size of the structures is exaggerated for illustrative purposes.)

Figure 3:
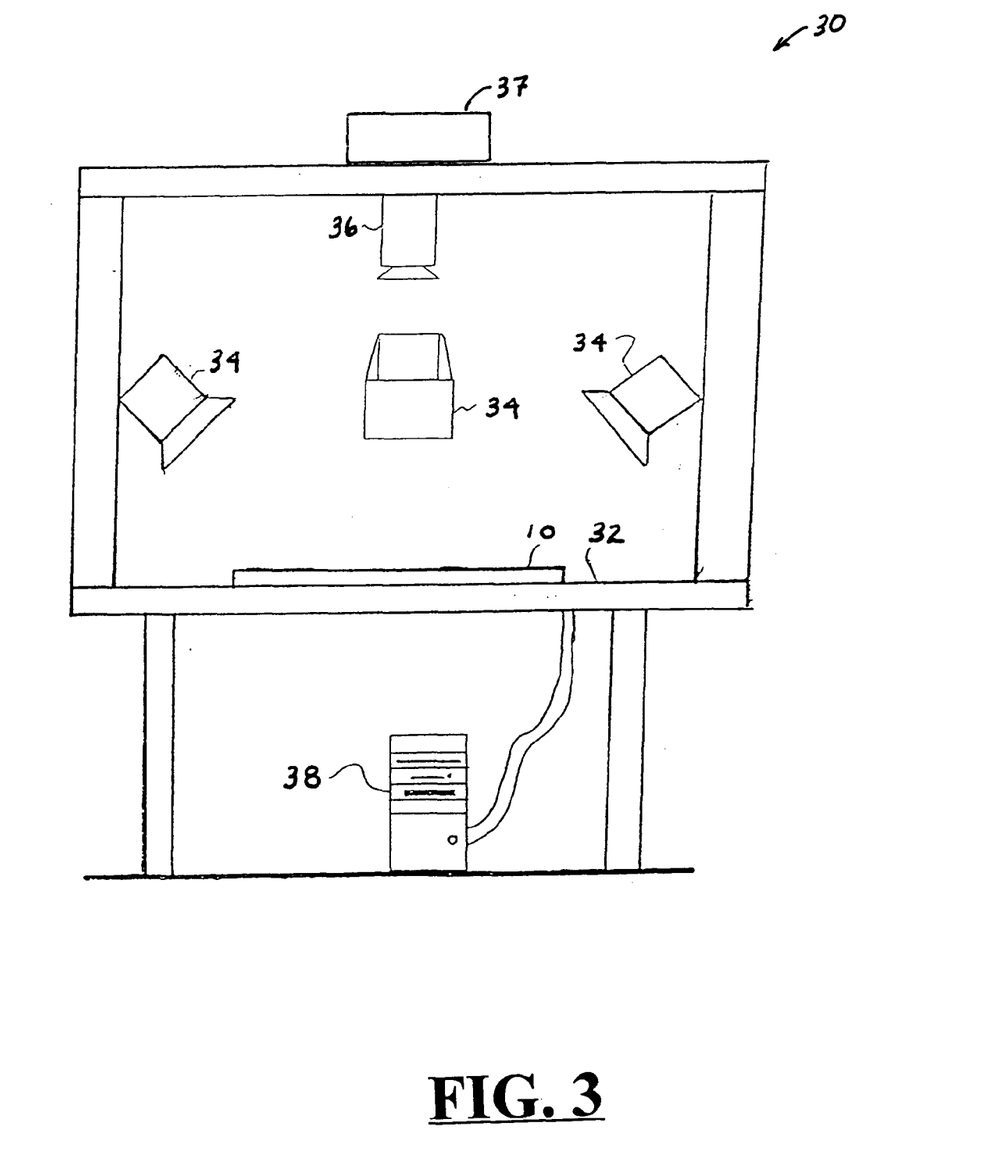
FIG. 3 is an elevation view of an inspection station for use in practicing the method of the present invention.

FIG. 3 is an elevation view of a semiconductor-wafer optical inspection station 30. Wafer 10 is held in place by inspection stand 32, which may also be constructed to be able to move the wafers into place or shift them during inspection. The wafer being inspected is illuminated by energy (often visible light) sources 34. Image capturing device 36, captures one or more images of illuminated wafer 10, which are then converted to a digital electronic format by digitizer 37. Digitizer 37 is connected to computer 38, which can be used for storing and analyzing the image data. Computer 38 may also be used for controlling the inspection stand 32 and energy sources 34, or for transmitting the collected data (or a representation of it) to any number of peripheral devices or other computers (not shown). In accordance with the present invention, computer 38 is programmed to perform wafer signature analysis, a process described more fully below. Of course, the digitized images can be reviewed, analyzed, and classified in a variety of ways, and the analysis described herein may be performed in addition to any number of other operations.

Figure 4:
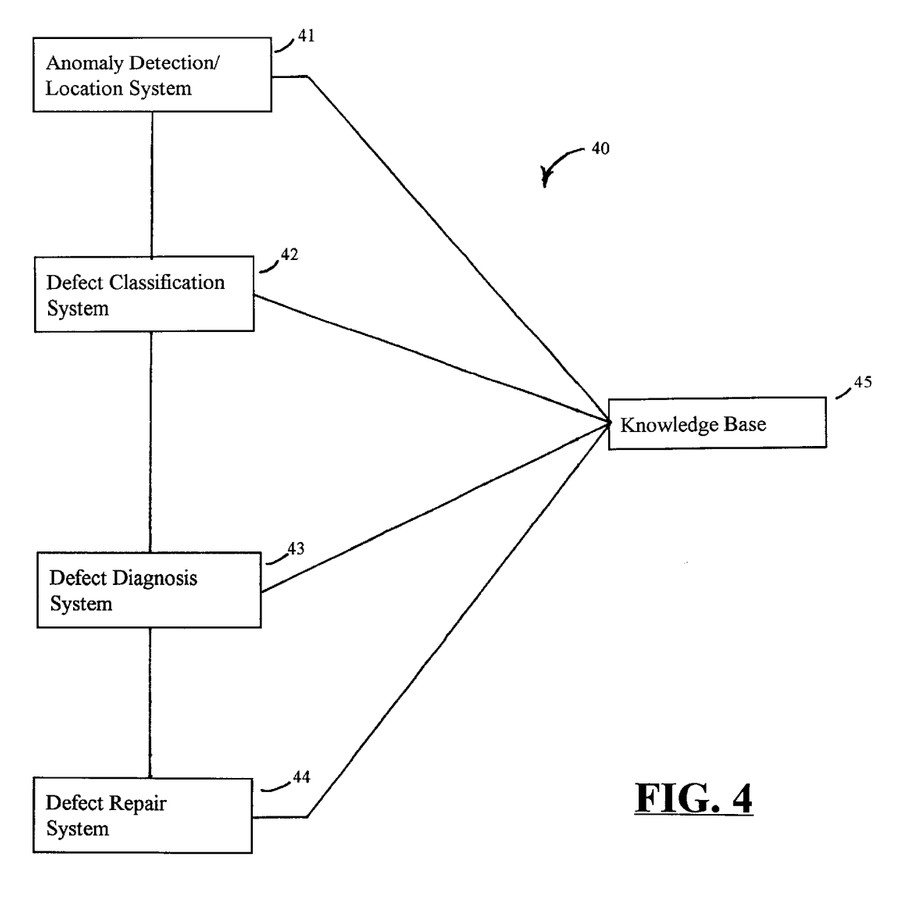
FIG. 4 is a functional block diagram of an integrated defect detection, classification, diagnosis, and repair system such as one for use in implementing the present invention.

In a preferred embodiment, the present invention is used as part of an optical Integrated Defect Detection, Classification, Diagnosis, and Repair (IDDCDR) system. FIG. 4 is a functional block diagram showing the basic components of a typical IDDCDR system 40. An anomaly detecting and locating inspection system 41 includes the actual components by which a manufactured object is positioned in a suitable environment, properly illuminated, and an image of the energy reflected off of the object is captured. Using this image, a defect classification system 42 determines the location and type of any anomaly detected (or determines that the anomaly is of a type not previously identified). Defect typing is performed with reference to a previously established (and continually supplemented) knowledgebase 45. After a defect has been found and categorized, a diagnosis system 43 attempts to identify the cause of the identified defect. Thereafter, suitable remedial action may be dictated by a defect repair system 44.

Figure 5:
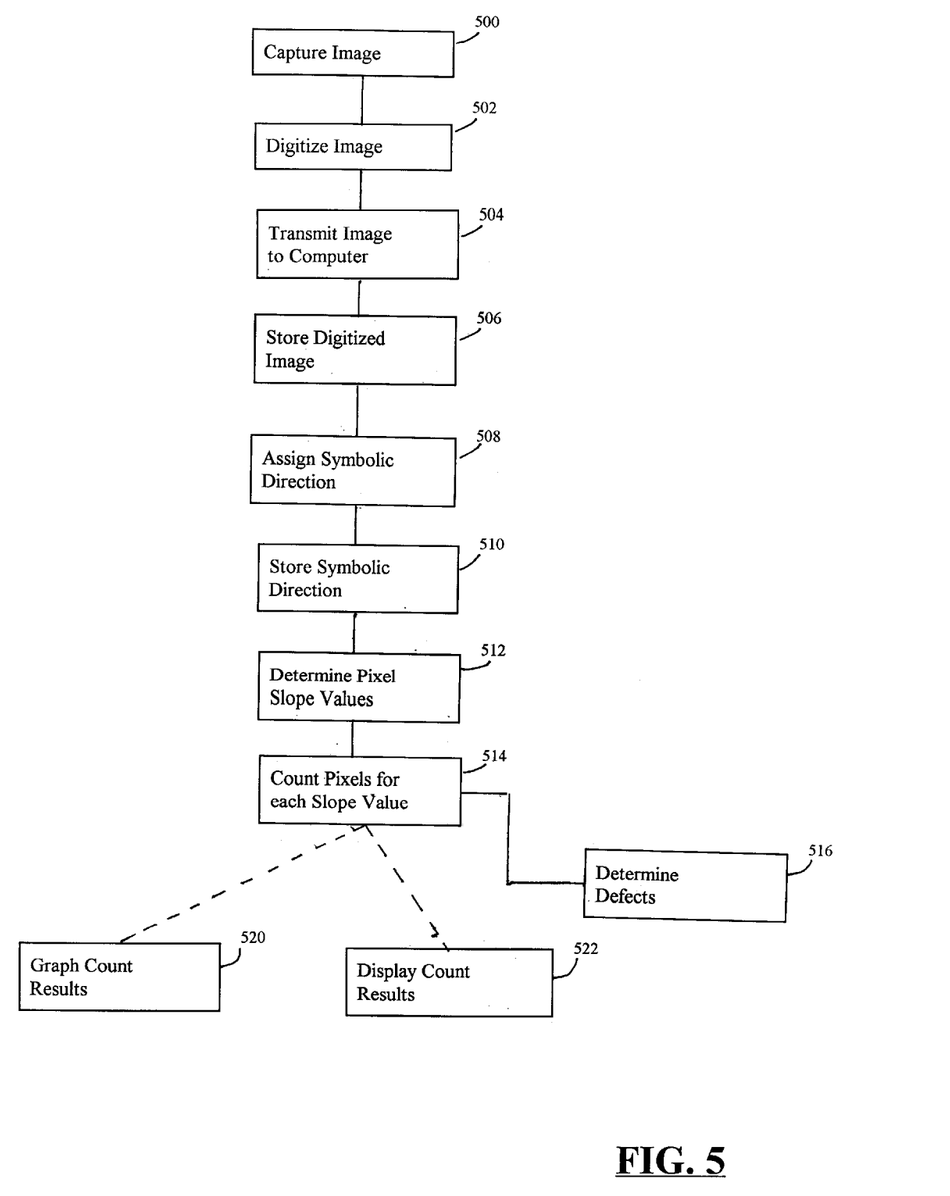
FIG. 5 is a flow diagram illustrating the method of inspection in accordance with one embodiment of the present invention.

FIG. 5 is a flow diagram depicting an embodiment of the wafer signature analysis method of the present invention. The process begins at step 500, where wafer 10 has been placed onto a support such as inspection stand 32, illuminated as desired, and an image of the wafer captured. Note that it is desirable but not necessary to capture an image of the entire wafer. If only a partial image is captured, however, this factor must be accounted for in the defect analysis. The desired portion usually encompasses that part of the wafer surface on which components are actually being constructed, and excludes vacant or unused portions. (For convenience, the terms "surface" or "wafer" will apply herein to either the entire wafer or to a selected portion thereof) The captured image is then digitized (step 502), that is, converted into a digital electronic form, and transmitted to computer 38 (step 504). Computer 38 then stores the digitized image in a database (step 506), such as knowledge base 45 shown in FIG. 4. The stored digital image can be referred to as a pixel image. Here, pixel is used to refer to the smallest separately identifiable component of a digitally stored pixel image, and the data associated with it, regardless whether the stored image is actually used or usable to produce a visual graphic image without further processing. In accordance with the present invention, the image can be divided in any number of pixels, but a satisfactory results have been obtained by dividing the image into 1000r×1000r pixels, with r representing the radius of the wafer. During digitization, each pixel is examined and a representative value assigned to the (light) intensity of the partial image it contains.

In an alternate embodiment (not shown), the pixel image of wafer 10 is actually a composite of several images captured and digitized separately, then assembled by the computer into a single pixel image. This may be done so that the wafer area captured in each separate image is smaller, resulting in greater resolution of the final image. Or several images of the same area may be taken and process to filter out the effects of inspection stand wobble, for example as disclosed in co-owned and co-pending U.S. patent application Ser. No. 09/262,603. Both techniques may also be used. In any event, the resulting pixel image of a complete wafer, or selected portion thereof, is stored in the computer 38 database at step 506. Note, however, that in order to practice the method of the present invention, it is not necessary to store pixel information about each area of wafer 10 in a single computer file, and certainly separate data sets can be maintained if addressable in order to properly perform the wafer signature analysis and classification.

The process then moves to step 508, the determination of pixel symbolic direction. This may be done, for example, using the process of symbolic decomposition, further described in co-pending U.S. patent applications Ser. Nos. 09/262,603 and 09/338,880. Basically, this process analyzes the pixel image and compiles a set of descriptors (called "primitives"), one for each structure (or in some cases shadow) edge. As a result, pixels situated along the image of a structure edge can be assigned a symbolic direction analogous to the orientation, in relation to the x-y axes, of the edge itself. In other words, each pixel is assigned as its symbolic direction the orientation of the structural (or shadow) edge of which the pixel is part. (Pixels associated with non-edge spaces on the wafer are ignored.) This process may be done for all pixels in the pixel image or for a selected group. The symbolic direction data is also stored in the database (step 510).

The method of this embodiment of the present invention then continues with a determination of pixel-slope values along a number of vectors (step 512). Each vector represents a line originating in the wafer center 13 and extending outward toward the nearest point on the periphery. There may be any number of such vectors used for this analysis, but the vectors used must form a symmetrical pattern about the wafer's x-y axes. Each set or group of vectors corresponds to a different type of defect. The pixel slope represents the angular difference between the vector orientation and that of the structure segment captured in the pixel. Preferably, vector orientation is determined in relation to the x-y coordinate system previously discussed. In this embodiment, the angular difference between the vector and the structure slope is always less than 90 degrees, that is, the smallest angle between the two intersecting lines is used. The sign of the slope can be assigned in any consistent method Next, the number of pixels having a value for each of a selected number of pixel slope angles is counted (step 514). It has been found that for wafers lacking certain kinds of photoresist defects, the total number of pixels having been assigned any given pixel-slope value will tend to a common value. Deviations from this norm may indicate the presence of defects, deviations being determined (step 516) by a human operator or by computer 38 after comparing the wafer signature to those recorded in the knowledge base 45. This is referred to as wafer defect classification. For example, spikes (relatively high pixel counts) around a 0° pixel slope value reveals a photoresist defect known as "streaking", where the photoresist material instead of spreading evenly tends to gather in a linear patterns extending outward from the wafer center 13. Spikes around the 90° pixel slope value, on the other hand, tend to reveal ring anomalies, where the uneven gathering of photoresist forms concentric rings around the center 13. Examples of each of these types of defects can be seen in the copies of photographs provided in the Appendix.

Note that ideally, properly developed photoresist would exhibit a straight line at the average or zero value, but the captured image often includes blank or unused portions of the wafer (see FIG. 1) that result in a somewhat undulating graph. Still the representation clearly illustrates the difference between a wafer having a properly formed photoresist and an anomalous one.

Figure 6A:
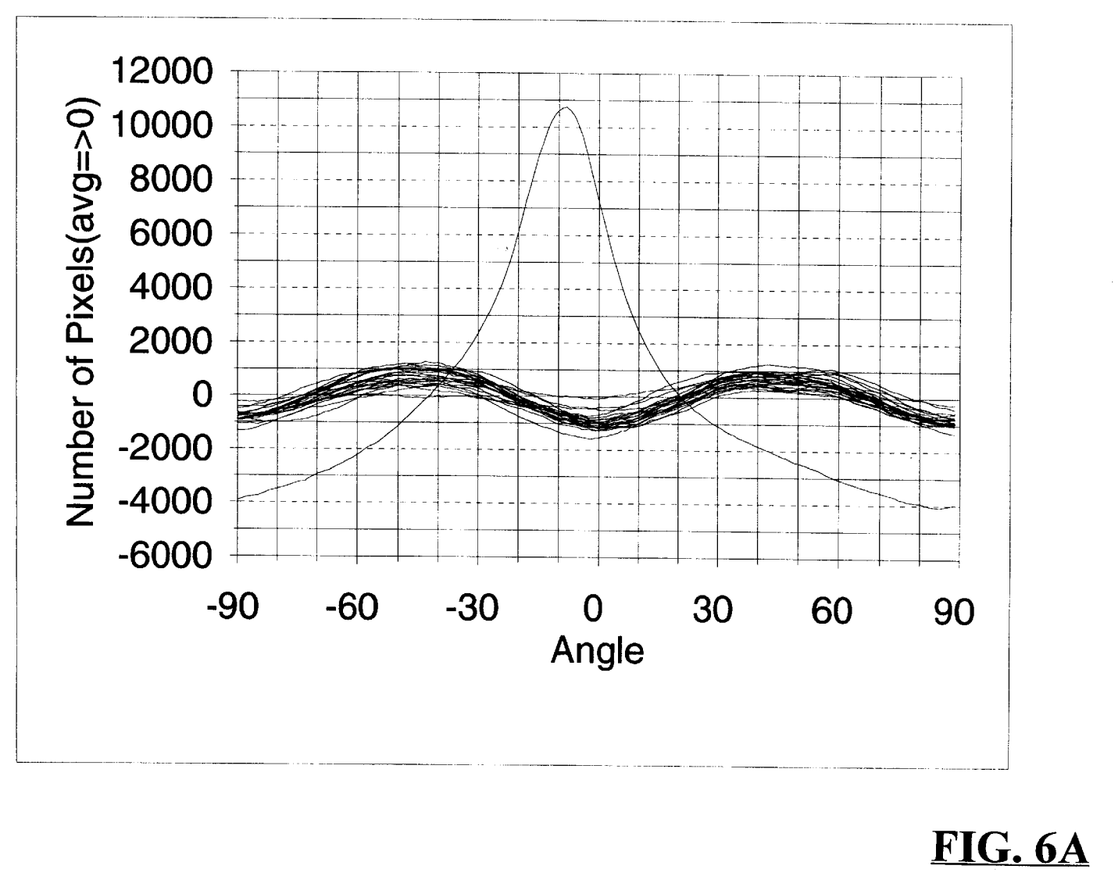
FIGS. 6A and 6B are graphical representations of pixel image data collated and displayed for visual analysis according to an embodiment of the present invention.
Figure 6B:
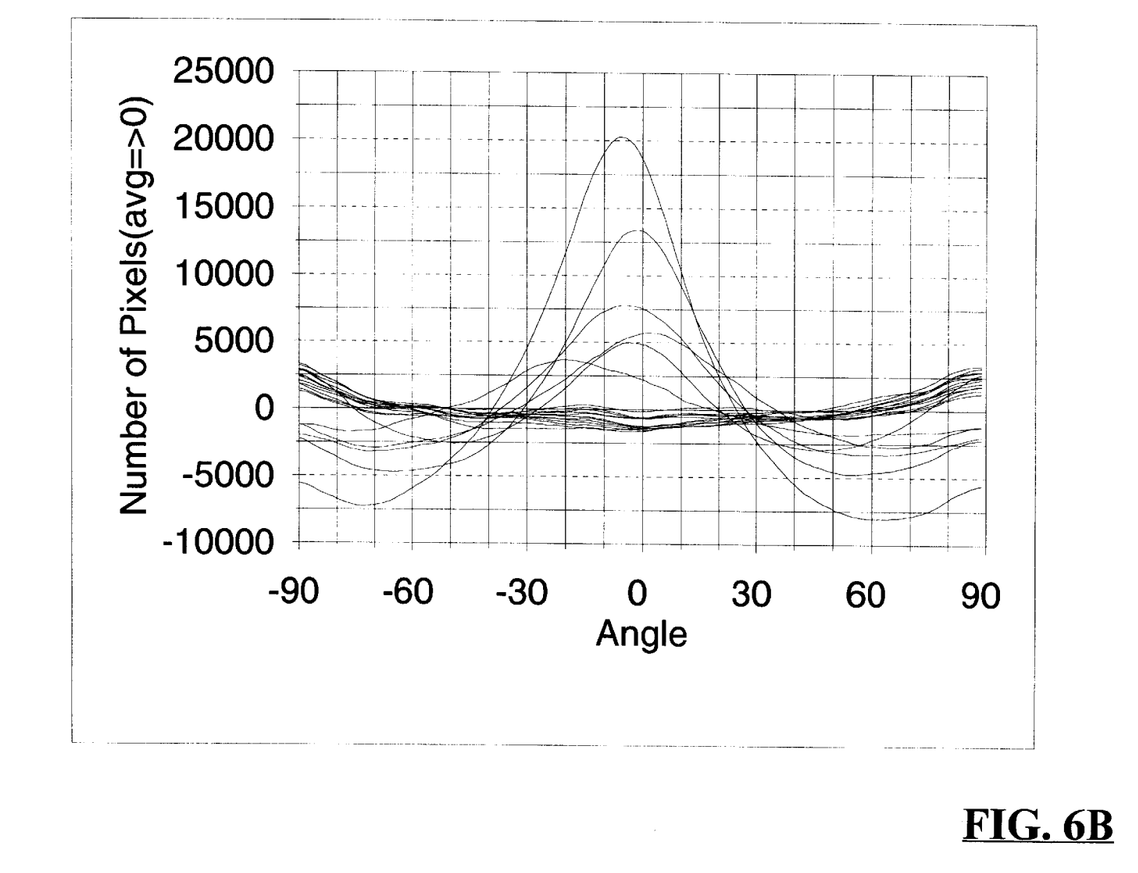

The pixel count data is then graphed (step 520) onto print media or displayed on a monitor (step 522). Of course, a visual graphic display is needed only where the information needs to be viewed by a human operator. It should be noted that this graphic representation can use an absolute number of pixels, or use an average number of pixels having the same slope to establish a 'zero', with other values plotted in relation to the zero or average value. See, for example, the exemplary graphs of FIGS. 6A and 6B.

Armed with this information, the wafer manufacturer can identify wafers exhibiting such defects and either discard them or take remedial action. When a non-familiar anomaly appears, it is added to the knowledge base for future reference.

Based on the foregoing description, one of ordinary skill in the art should readily appreciate that the present invention advantageously provides an efficient system and method of detecting defects present on structure-bearing surfaces of objects.

It is thus believed that the operation and construction of the present invention will be apparent from the foregoing description. While the system and method shown and described has been characterized as being preferred, it will be readily apparent that various changes and modifications could be made therein without departing from the scope of the invention as defined in the following claims.

What is claimed is:

1. A method of detecting defects on a structure-bearing surface of an object using a captured image that has been digitized, comprising the steps of:

determining the symbolic direction of each of a first preselected group of pixels in the digitized image;

assigning a pixel-slope value to each of a second preselected group of pixels, wherein the second preselected group of pixels are those pixels in the first preselected group that are disposed along one of a plurality of vectors emanating outwardly from a point defined by the intersection of a horizontal axis and a vertical axis, wherein the plurality of vectors are symmetrically distributed about the horizontal axis and the vertical axis and wherein the pixel-slope value represents the angular difference between the symbolic direction of the pixel and the vector on which the pixel is disposed;

counting the number of pixels having a pixel-slope value equal to each of a plurality of preselected pixel-slope values; and comparing the relative number of pixels assigned to each pixel-slope value in order to determine whether a defect is present.

2. The method of claim 1, further comprising the step of comparing the pixel-count distribution to at least one corresponding reference distribution in the event that a defect is detected, in order to determine whether the wafer defect corresponds to a known condition.

3. The method of claim 1, further comprising the step of producing a visual graphical plot of the number of pixels corresponding to given pixel-slope values.

* * * * *